United States Patent
Spanuth

(10) Patent No.: US 7,432,107 B2
(45) Date of Patent: Oct. 7, 2008

(54) CARDIAC HORMONES FOR ASSESSING CARDIOVASCULAR RISK

(75) Inventor: Eberhard Spanuth, Dossenheim (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 11/297,923

(22) Filed: Dec. 8, 2005

(65) Prior Publication Data

US 2006/0234300 A1 Oct. 19, 2006

Related U.S. Application Data

(63) Continuation-in-part of application No. 11/041,671, filed on Jan. 24, 2005.

(51) Int. Cl.
G01N 33/00 (2006.01)
G01N 33/53 (2006.01)

(52) U.S. Cl. .................................. 436/87; 436/817

(58) Field of Classification Search .................. None
See application file for complete search history.

(56) References Cited

U.S. PATENT DOCUMENTS

2003/0022235 A1 1/2003 Dahlen et al.

FOREIGN PATENT DOCUMENTS

| WO | WO 02/083913 A1 | 10/2002 |
|---|---|---|
| WO | WO 02/089657 A2 | 11/2002 |

OTHER PUBLICATIONS

Wells et al. Additivity of Mutational Effects in Proteins; Biochemistry, vol. 29, No. 37 (1990) pp. 8509-8517.*
Seffernick et al. Melamine Deaminase and Atrazine Chlorohydrolase: 98 Percent Identical but Functionally Different; Journal of Bacteriology, vol. 183, No. 8 (2001) pp. 2405-2410.*
Minter et al. The Clycooxygenase 2-Selective Inhibitor NS398 Inhibits Proliferation of Oral Carcinoma Cell Lines by Mechanisms Dependent and Independent of Reduced Protaglandin E2 Synthesis; Clinical Cancer Research, vol. 9 (2003) pp. 1885-1897.*
Bibbins-Domingo et al. B-Type Natriuretic Peptide and Ischemia in Patients With Stable Coronary Disease; Circulation, vol. 108 (2003) pp. 2987-2992.*
Bazzino et al. Relative Value of N-Terminal Probrain Natriuretic Peptide, TIMI Risk Score, ACC/AHA Prognostic Classification and Other Risk Markers in Patients With Non-ST-Elevation Acute Coronary Syndromes; European Heart Journal, vol. 25 (2004) pp. 859-866.*
Giannitsis, E. Rationale for Testing the Cardiovascular Risk for Patients With Cox-2 Inhibitors on the Basis of Biomarker NT-PROBNP; Clinical Laboratory, vol. 51, No. 1-2(2005) pp. 63-72.*
Bombardier, Claire, et al., "Comparison of Upper Gastrointestinal Toxicity of Rofecoxib and Naproxen in Patients with Rheumatoid Arthritis," The New England Journal of Medicine, vol. 343, No. 21, Nov. 23, 2000, p. 1520-1528.

FitzGerald, Garret A. et al., "Coxibs and Cardiovascular Disease," New England Journal of Medicine 351; 17, Oct. 21, 2004, p. 1709-1711.
Juni, Peter et al., "Risk of cardiovascular events and rofecoxib: cumulative meta-analysis," www.thelancet.com; vol. 364, Dec. 4, 2004, p. 2021-2029.
Topol, Eric J. et al., "Failing the Public Health—Rofecoxib, Merk, and the FDA," New England Journal of Medicine 331;17, Oct. 21, 2004, 1707-1709.
Mukherjee, Debabrata, et al., "Risk of Cardiovascular Events Associated with Selective COX-2 Inhibitors," JAMA, Aug. 22/29, 2001-vol. 286, No. 8, p. 954-959.
Ambrose, T., "Review of the Clinical Utility of NT-proBNP in the Diagnosis, Prognosis and Therapy Monitoring of Patients with Congestive Heart Failure," Journal of Clinical Ligand Assay 25:2, Summer 2002, 160-166.
Bazzino, O. et al., "Relative value of N-terminal probrain natriuretic peptide, TIMI risk score, ACC/AHA prognostics classification and other risk markers in patients with non-ST-elevation acute coronary syndromes," European Heart Journal (2004) 25, 859-866.
Bibbins-Domingo, K. et al., "B-Type Natriuretic Peptide and Ischemia in Patients with Stable Coronary Disease: Data From the Heart and Soul Study," Circulation, Journal of the American Heart Association,Dec. 16, 2003, 2987-2992.
Masson, S. et al., "Comparative Measurement of N-Terminal Pro-Brain Natriuretic Peptide and Brain Natriuretic Peptide in Ambulatory Patients with Heart Failure," Clin. Chem. Lab Med 2002; 40(8) 761-763.
Minter, H. et al., "The Cyclooxygenase 2-selective Inhibitor NS398 Inhibits Proliferation of Oral Carcinoma Cell LInes by Mechanisms Dependent and Independent of Reduced Prostaglandin E2 Synthesis," Clinical Cancer Research Review, vol. 9, 1885-1897, May 2003.

(Continued)

Primary Examiner—Jon P Weber
Assistant Examiner—Paul C Martin
(74) Attorney, Agent, or Firm—Mariln L. Amick; Roche Diagnostics Operations, Inc.

(57) ABSTRACT

The present invention relates to the use of cardiac hormones, particularly natriuretic peptides, for diagnosing the cardiovascular risk of a patient who is a candidate for administration of a cox-2-inhibiting compound, in particular an NSAID, selective cox-2 inhibitor, or steroid. More particularly, the present invention relates to the use of cardiac hormones, particularly natriuretic peptides, for diagnosing the cardiovascular risk of a patient who is a candidate for administration of a selective cox-2 inhibitor, comprising the steps of (a) measuring, preferably in vitro, the level of a cardiac hormone, (b) diagnosing the risk of the patient by comparing the measured level to known levels associated with different grades of risk in a patient. The most preferred cardiac hormone in the context of the present invention is NT-proBNP. Furthermore, the present invention relates to a method for diagnosing the risk of a patient to suffer from a cardiovascular complication as a consequence of administration of a cox-2 inhibiting compound, comprising the steps of (a) measuring the level of a cardiac hormone, (b) diagnosing the risk of the patient by comparing the measured level to known levels associated with different grades of risk in a patient.

15 Claims, 4 Drawing Sheets

OTHER PUBLICATIONS

Mamdani, M. et al., "Cyclo-oxygenase-2 Inhibitors Versus Non-Selective Non-Steroidal Anti-Inflammatory Drugs and Congestive Heart Failure Outcomes in Elderly Patients: a Population-based Cohort Study," The Lancet, vol. 363, May 29, 2004, 1751-1756.

Pfister, R. et al., "Use of NT-proBNP in routine testing and comparison to BNP," The European Journal of Heart Failure 6 (2004) 289-293.

Ruskoaho, H., "Cardiac Hormones as Diagnostics Tools in Heart Failure," Endocrine Reviews 2(3) 341-356, 2003.

Seffernick, J. et al., "Melamine Deaminase and Atrazine Chlorohydrolase: 98 Percent Identical but Functionally Different," Journal of Bacteriology 183:8 Apr. 2001, 2405-2410.

Wells, J., "Perspectives in Biochemistry," Biochemistry 29:37 (Sep. 18, 1990) 8509-8517.

* cited by examiner

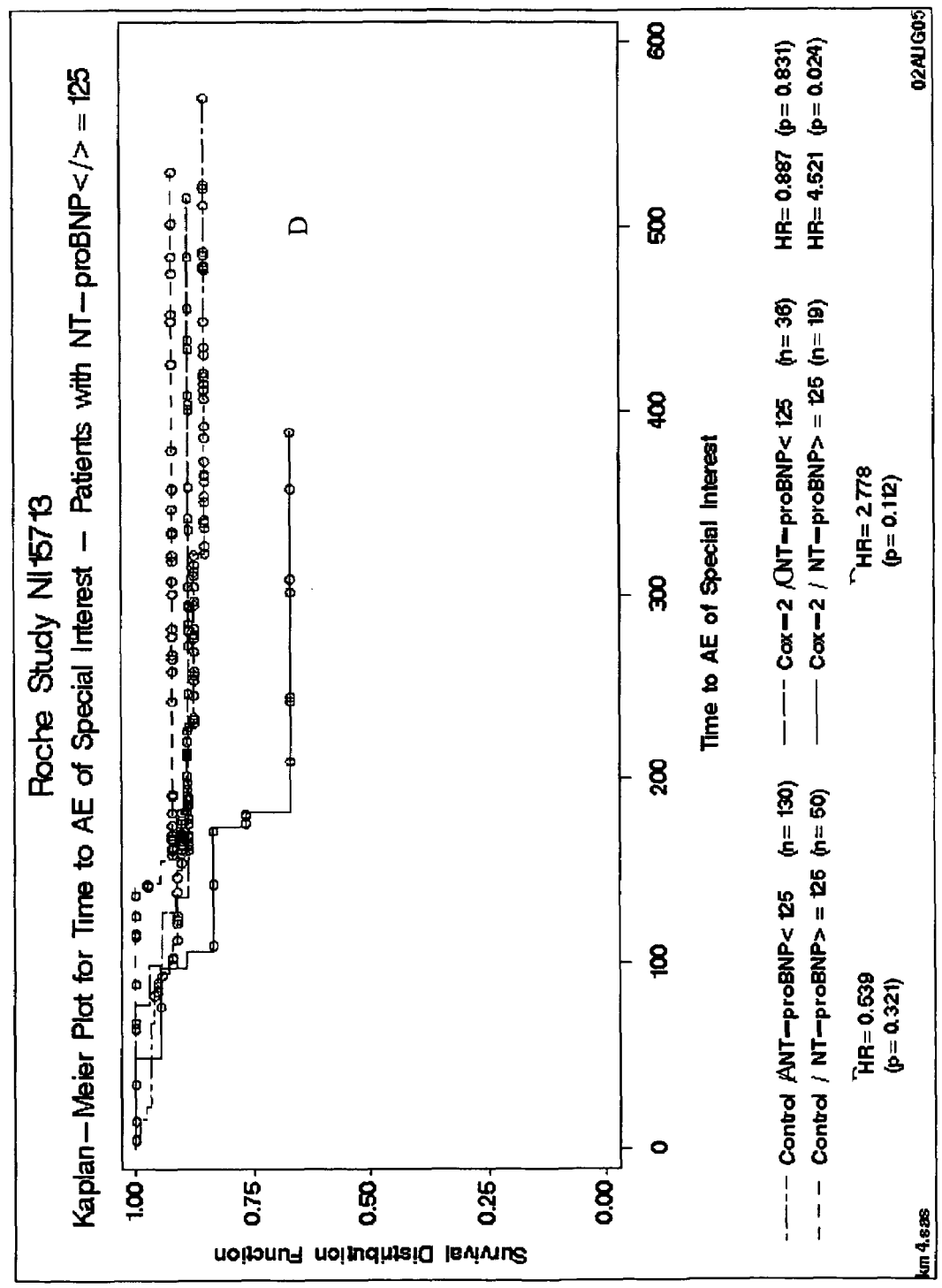

CARDIAC HORMONES FOR ASSESSING CARDIOVASCULAR RISK

RELATED APPLICATIONS

This application is a continuation-in-part of U.S. Ser. No. 11/041,671 filed Jan. 24, 2005.

FIELD OF THE INVENTION

The present invention relates to the use of cardiac hormones for assessing the cardiovascular risk of a patient with respect to the administration of an anti-inflammatory drug, particularly NSAIDs (non-steroidal anti-inflammatory drugs) or steroids, more particularly selective cox-2 (cyclooxygenase-2) inhibitors.

BACKGROUND OF THE INVENTION

An aim of modem medicine is to provide personalized or individualized treatment regimens. Those are treatment regimens which take into account a patient's individual needs or risks. Of particular importance is the cardiovascular risk or complication, particularly an unrecognized cardiovascular risk or complication.

Selective cox-2 inhibitors are widely used potent anti-inflammatory drugs. Compared to many other anti-inflammatory drugs, they appear to cause less gastrointestinal side-effects, such as gastrointestinal bleeds or ulcers. Therefore, for many patients treatment with selective cox-2 inhibitors is the treatment of choice.

However, it has been noted recently, that selective cox-2 inhibitors can lead to cardiovascular complications, possibly followed by cardiac decompensation and even death. Rofecoxib (VIOXX™), a selective cox-2 inhibitor, was only recently removed from the market voluntarily by the manufacturing company, Merck, after a 3.9 times rise in the rate of serious thromboembolic incidents had led to premature discontinuation of the APPROVE study (Adenomatous Polyp Prevention On Vioxx). Only patients without any recognisable cardiovascular risk were included in that study for the secondary prevention of colon adenomas. Even in the early post-observation phase higher blood pressure levels had been noticed with 25 mg rofecoxib than with a placebo. 16 additional cardiovascular incidents per 1,000 treated patients (myocardial infarction, stroke) with 25 mg rofecoxib compared with a placebo (Topol E J. Failing the public health—rofecoxib, Merck, and the FDA. N Engl J Med 2004; 351: 1707-9) were noticed after 18 months of follow-up. An increased cardiovascular risk has also been suspected in other studies (VIGOR) and has been supported by data from a recent meta-analysis (Bombardier C, Laine L, Reicin A, Shapiro D, Burgos-Vargas R, Davis B, Day R, Ferraz M B, Hawkey C J, Hochberg M C, Kvien T K, Schnitzer T J; VIGOR Study Group. Comparison of upper gastrointestinal toxicity of rofecoxib and naproxen in patients with rheumatoid arthritis. VIGOR Study Group. N Engl J Med 2000; 343: 1520-8; Jüni P, Nartey L, Reichenbach S, Sterchi R, Dieppe P A, Egger M. Risk of cardiovascular events and rofecoxib: cumulative meta-analysis. Lancet 2004; online ahead).

Similar cardiovascular side-effects are suspected within the scope of a class effect for other selective cyclooxygenase-2 inhibitors such as celecoxib (Celebrex™, Pfizer), lumiracoxib (Prexige™, Novartis) and parecoxib, a pro-drug of valdecoxib, although at a lower incidence rate (Fitzgerald G A. Coxibs and cardiovascular disease. N Engl J Med 2004; 351: 1709-1711. Mukheijee D, Nissen S E, Topol E J. Risk of cardiovascular events associated with selective COX-2 Inhibitors. JAMA 2001; 286: 954-959.).

Cardiovascular complications, such as acute myocardial infarction or stroke, may lead to serious health problems and even death. Therefore, many patients who would strongly benefit from treatment with selective cox-2 inhibitors are not treated as it is unknown whether treatment may result in a cardiovascular complication.

Cardiovascular problems or risks can remain asymptomatic for long periods of time. Therefore, reliable diagnosis of the presence of a cardiovascular risk is more difficult and error-prone than generally believed. In particular, general practitioners and non-cardiologists often are not able to identify a previously unrecognized cardiovascular problem.

According to the state of the art, it is only possible to exclude patients with cardiovascular symptoms or a known history of heart disease or hypertension from treatment with selective cox-2 inhibitors.

This risk management is insufficient, as also asymptomatic patients may develop a cardiovascular complication due to an unrecognized predisposition, e.g. the presence of an arterial plaque. As mentioned earlier, only patients without any recognisable cardiovascular risk were included in the APPROVE study, yet treatment led to cardiovascular complications in several patients.

In the prior art, no hint is given how the risk of a cardiovascular complication associated with treatment with an anti-inflammatory drug, in particular a selective cox-2 inhibitor can be diagnosed. Particularly, no reference has been made how such diagnosis can be made in patients that have no known history of cardiovascular complications.

This does not only apply with respect to selective cox-2 inhibitors, but also with respect to other classes of anti-inflammatory drugs, e.g. being inhibitors of cox-2 and other target (e.g. Cox-1), and which may cause cardiovascular complications. Examples for these other classes of anti-inflammatory drugs include non-selective cox-2 inhibitors (compounds inhibiting Cox-1 and cox-2). Even though the risk of leading to cardiovascular complications is not as high as for selective cox-2 inhibitors, there may be cases where a possible cardiovascular complication has to be taken into account.

For example, cardiovascular side-effects are also suspected for other anti-inflammatory drugs, in particular other NSAIDs or steroids.

Therefore, there is a need to for a method or means to identify risk patients before they receive treatment with anti-inflammatory drugs, particularly NSAIDs or steroids, more particularly selective cox-2 inhibitors. Particularly, there is a need to provide a suitable diagnostic means. Particularly, there is a need for a diagnostic means that allows to identify risk patients that have no history or no known history of a cardiovascular risk or complication. In particular, the diagnostic means should be reliable and suited for use by general practitioners and non-cardiologists.

SUMMARY OF THE INVENTION

The object of the invention is attained by a method for diagnosing the risk of a patient to suffer from a cardiovascular complication as a consequence of administration of an anti-inflammatory drug, particularly an NSAID, steroid, or a selective cox-2 inhibitor, comprising the steps of measuring the level of a cardiac hormone and diagnosing the risk of the patient by comparing the measured level to known levels associated with different grades of risk in a patient.

The object of the invention is furthermore attained by a method for diagnosing the cardiovascular risk of a patient who is a candidate for administration of a compound having cox-2 inhibiting properties, comprising the steps of measuring, preferably in vitro, the level of a cardiac hormone and diagnosing the risk of the patient by comparing the measured level to known levels associated with different grades of risk in a patient.

The compound having cox-2 inhibiting properties (also referred to as cox-2 inhibitor) can also be any compound having anti-inflammatory properties (e.g. it can be a steroid or NSAID). Most preferably, the compound is a selective cox-2 inhibitor.

The object of the invention is also attained by a method of deciding on the possible treatment of a patient with a compound having cox-2 inhibiting properties, which method comprises measuring, preferably in vitro, the level of a cardiac hormone in the patient, comparing the measured level with known levels associated with different grades of risk in a patient, optionally initiating an examination of the patient by a cardiologist, recommending the initiation of the treatment or refraining from the treatment, optionally in consideration of the result of the patient's examination by the cardiologist.

BRIEF DESCRIPTION OF THE DRAWINGS

FIG. 4: This figure refers to Example 5. Kaplan-Meier curve based on cardiologist adjudicated cardiovascular (CV) adverse events (AE) for cox-2 inhibitors group and comparison group with NT-proBNP<125 pg/ml vs.>125 pg/ml. FIG. 4 shows the same results as indicated in FIG. 3 using a NT-proBNP cut-off value of 125 pg/ml. AE, adverse event; n, number; HR, hazard ratio; p, probability; survival distribution function, event-free survival distribution function.

DETAILED DESCRIPTION OF THE INVENTION

Figure 1:
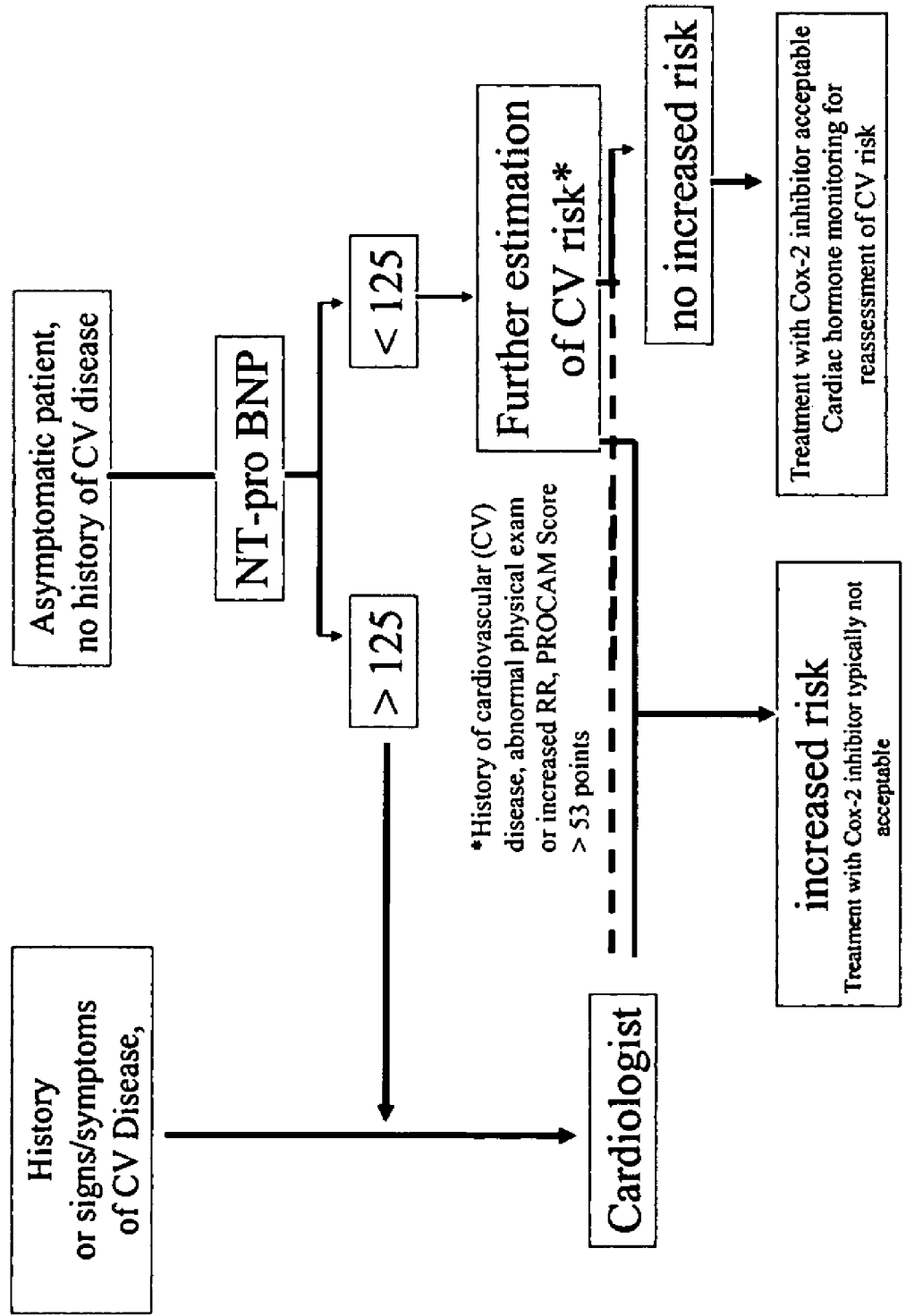
FIG. 1: Flow chart of an example of the invention. Patients who are candidates for receiving an anti-inflammatory drug (e.g. a cox-2 inhibitor) are grouped into patients without and patients with symptoms of cardiovascular disease (CV). If the measured plasma level of NT-proBNP is above the chosen cut-off of 125 pg/ml, the patient is referred to a cardiologist. If the measured level of the cardiac hormone is below the chosen cut-off (e.g. a plasma level of 125 pg/ml NT-proBNP), the patient is subjected to a limited physical examination (e.g. establishing the PROCAM score or Framingham score, anamnesis, blood pressure (RR), possibly electrocardiogram). If the result from the physical examination does not indicate a cardiovascular risk, the anti-inflammatory drug is administered, but the patient receives monitoring of the level of the cardiac hormone. The cardiologist plays a major role in evaluating all risk indicators and treatment options.

The compound having cox-2 inhibiting properties (also referred to as cox-2 inhibitor) can also be any compound having anti-inflammatory properties (e.g. it can be a steroid or NSAID). Most preferably, the compound is a selective cox-2 inhibitor.

From what was said earlier, it is evident that the methods are preferably carried out before the compound in question is administered.

The methods may also comprise the step of taking a body fluid or tissue sample from the patient. Within the present invention, the taking of the said body fluid or tissue sample can preferably be carried out by non-medical staff (i.e. not having an education necessary for carrying out the profession of a physician). This applies in particular when the body sample is blood.

The object of the invention is also attained by use of a diagnostic means for measuring, preferably in vitro, a patient's level of a cardiac hormone, particularly a natriuretic peptide, for diagnosing the cardiovascular risk of a patient who is a candidate for administration, particularly future administration, of a compound having cox-2 inhibiting properties. Preferably the level is determined in a body fluid or tissue sample of the patient.

The compound having cox-2 inhibiting properties (also referred to as cox-2 inhibitor) can also be any compound having anti-inflammatory properties (e.g. it can be a steroid or NSAID). Most preferably, the compound is a selective cox-2 inhibitor.

The present invention provides simple and inexpensive methods and means to screen patients who are about to receive medication with a compound having cox-2 inhibiting properties, particularly a selective cox-2 inhibitor for their risk of developing a cardiovascular complication as a consequence of said medication. Said medication may comprise any anti-inflammatory drug or compound having cox-2 inhibiting properties, in particular an NSAID, steroid, selective cox-2 inhibitor, or any combination thereof. For example, said medication may comprise combined treatment with a steroid and a selective cox-2 inhibitor or it may comprise combined treatment with a selective cox-2 inhibitor and another NSAID (see also Example 5). The present invention also provides levels of cardiac hormones indicating the existence or severity of a cardiovascular risk in patients with or without obvious symptoms of a cardiovascular disorder.

It may be assumed that patients with a cardiovascular disorder in their case history (myocardial infarction, unstable angina pectoris, coronary artery disease, heart failure, CABG (coronary artery bypass graft), stroke) or patients with an underlying inflammatory disorder such as chronic polyarthritis, osteoarthritis, or rheumatoid arthritis or other rheumatoid disorders are predisposed to the occurrence of cardiovascular complications. In rheumatoid arthritis, the cardiovascular death rate is particularly high for various reasons.

The use of cardiac hormones and natriuretic peptides as molecular or biochemical markers is known as such. In WO 02/089657, it has been suggested to measure brain natriuretic peptide (BNP) to diagnose various myocardial dysfunctions. In WO 02/083913 it has been suggested to use BNP to predict near-term morbidity or mortality in patients with non-ST-elevated acute coronary syndromes. In a previously unpublished European application (EP 1 577 673 A1) it has been suggested to use natriuretic peptides to diagnose the risk of a patient of suffering from a cardiovascular complication as a consequence of an increase of intravasal volume.

The present invention is particularly advantageous to general practitioners, specialized physicians, and specialized wards, departments, or clinics which frequently have no access to extensive cardiological examination by cardiologists. The present invention provides means and methods to such non-cardiologists for simple and reliable screening of patients and identification of those patients who are posed at a cardiovascular risk with respect to administration of a Cox-inhibitor or an anti-inflammatory drug, in particular with respect to administration of an NSAID, steroid, or a selective cox-2 inhibitor. Preferably, the decision about continuing or initiating treatment with the cox-2 inhibitor, in particular the NSAID, steroid, or selective cox-2 inhibitor, will be made by a physician. More preferably, the decision about continuing or initiating treatment with the cox-2 inhibitor, in particular the NSAID, steroid, or selective cox-2 inhibitor, will be made by a cardiologist or after consulting a cardiologist. This in particular applies in cases where high levels of the cardiac hormone(s) or natriuretic peptide(s) are measured. In cases in which the patient is diagnosed to have no cardiovascular risk, a decision to continue or initiate treatment with a cox-2 inhibiting compound, particularly an NSAID, steroid, or selective cox-2 inhibitor, may be made by a physician other than a cardiologist.

The invention takes advantage of certain biochemical or molecular markers. The terms "biochemical marker" and "molecular marker" are known to the person skilled in the art. In particular, biochemical or molecular markers are gene expression products which are differentially expressed (i.e. upregulated or downregulated) in presence or absence of a certain condition, disease, or complication. Usually, a molecular marker is defined as a nucleic acid (such as an mRNA), whereas a biochemical marker is a protein or peptide. The level of a suitable biochemical or molecular marker can indicate the presence or absence of the condition, disease, risk, or complication, and thus allow diagnosis.

The present invention particularly takes advantage of natriuretic peptides as biochemical markers. It should be noted that natriuretic peptides may be secreted in response to ischemia. Furthermore, taking advantage of combinations of any natriuretic peptides as biochemical markers is considered in the context of the present invention.

Natriuretic peptides according to the present invention comprise ANP-type and BNP-type peptides and variants thereof (see e.g. Bonow, R. O. (1996). New insights into the cardiac natriuretic peptides. Circulation 93: 1946-1950).

ANP-type peptides comprise pre-proANP, proANP, NT-proANP, and ANP.

BNP-type peptides comprise pre-proBNP, proBNP, NT-proBNP, and BNP.

The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP).

Preferred natriuretic peptides according to the present invention are NT-proANP, ANP, NT-proBNP, BNP, and variants thereof. ANP and BNP are the active hormones and have a shorter half-life than their respective inactive counterparts, NT-proANP and NT-proBNP. BNP is metabolised in the blood, whereas NT-proBNP circulates in the blood as an intact molecule and as such is eliminated renally. The in-vivo half-life of NT-proBNP is 120 min longer than that of BNP, which is 20 min (Smith M W, Espiner E A, Yandle T G, Charles C J, Richards A M. Delayed metabolism of human brain natriuretic peptide reflects resistance to neutral endopeptidase. J Endocrinol. 2000; 167: 239-46.).

Preanalytics are more robust with NT-proBNP allowing easy transportation of the sample to a central laboratory (Mueller T, Gegenhuber A, Dieplinger B, Poelz W, Haltmayer M. Long-term stability of endogenous B-type natriuretic peptide (BNP) and amino terminal proBNP (NT-proBNP) in frozen plasma samples. Clin Chem Lab Med 2004; 42: 942-4.). Blood samples can be stored at room temperature for several days or may be mailed or shipped without recovery loss. In contrast, storage of BNP for 48 hours at room temperature or at 4° Celsius leads to a concentration loss of at least 20% (Mueller T, Gegenhuber A, et al., Clin Chem Lab Med 2004; 42: 942-4, supra; Wu A H, Packer M, Smith A, Bijou R, Fink D, Mair J, Wallentin L, Johnston N, Feldcamp C S, Haverstick D M, Ahnadi C E, Grant A, Despres N, Bluestein B, Ghani F. Analytical and clinical evaluation of the Bayer ADVIA Centaur automated B-type natriuretic peptide assay in patients with heart failure: a multisite study. Clin Chem 2004; 50: 867-73.).

Therefore, depending on the time-course or properties of interest, either measurement of the active or the inactive forms of the natriuretic peptide can be advantageous. The most preferred natriuretic peptides according to the present invention are NT-proBNP or variants thereof.

The term "variants" in this context relates to peptides substantially similar to said peptides. The term "substantially similar" is well understood by the person skilled in the art. In particular, a variant may be an isoform or allele which shows amino acid exchanges compared to the amino acid sequence of the most prevalent peptide isoform in the human population. Preferably, such a substantially similar peptide has a sequence similarity to the most prevalent isoform of the peptide of at least 80%, preferably at least 85%, more preferably at least 90%, most preferably at least 95%. Substantially similar are also proteolytic degradation products which are still recognized by the diagnostic means or by ligands directed against the respective full-length peptide.

The term "variant" also relates to a post-translationally modified peptide such as glycosylated peptide. A "variant" is also a peptide which has been modified after collection of the sample, for example by covalent or non-covalent attachment of a label, particularly a radioactive or fluorescent label, to the peptide.

Other embodiments of the invention include the measuring of different cardiac hormones in combination, simultaneously or non-simultaneously. For example, measuring different cardiac hormones can yield important additional information, e.g. on the time-course of a developing cardiovascular complication. Therefore, the present invention also relates to measuring both an ANP-type peptide, or a variant thereof, and a BNP-type peptide, or a variant thereof.

The term "diagnosing" is known to the person skilled in the art. Diagnosing is understood as becoming aware of a particular medical condition, disease, complication, or risk. Diagnosing may also be understood as detecting or determining the presence of a particular medical condition, disease, complication, or risk. Diagnosing according to the present invention also includes monitoring, confirmation, subclassification and prediction of the relevant disease, complication, or risk. Monitoring relates to keeping track of an already diagnosed risk or complication, e.g. to analyze an elevation or decrease of the risk or the influence of a particular treatment on the elevation or decrease of the risk. Confirmation relates to the strengthening or substantiating a diagnosis already performed using other indicators or markers. Subclassification relates to further defining a diagnosis according to different subclasses of the diagnosed disease risk, e.g. defining according to increased risk or highly increased risk. Prediction relates to assessing a cardiovascular risk before other symptoms or markers have become evident or have become significantly altered.

Individuals suffering from a cardiovascular disease can be individuals suffering from stable angina pectoris (SAP) and individuals with acute coronary syndromes (ACS). ACS patients can show unstable angina pectoris (UAP) or these individuals have already suffered from a myocardial infarction (MI). MI can be an ST-elevated MI or a non-ST-elevated MI. The occurring of an MI can be followed by a left ventricular dysfunction (LVD). Finally, LVD patients undergo congestive heart failure (CHF) with a mortality rate of roughly 15%.

Furthermore, individuals suffering from a cardiovascular complication can be individuals suffering from stroke. The term "stroke" relates to any cerebro-vascular event in which blood flow to small or large regions of the brain is interrupted, e.g due to haemorrhage into the brain or a thrombosis of a cerebral artery. A stroke may result in temporary loss of consciousness or paralysis. In this case, the stroke is termed "apoplectic stroke".

The individuals may show clinical symptoms (e.g. dyspnea, chest pain, see also NYHA classification below) and they may be asymptomatic. Although the present invention is particularly advantageous to identify risk patients showing no symptoms of a preexisting cardiovascular disease, risk, or complication, it is also useful in other settings, e.g to confirm or monitor the risk status of the patient showing symptoms of a cardiovascular disease.

The term "cardiovascular risk" relates to the risk of developing a cardiovascular complication.

The present invention relates to "cardiovascular complications" developing as a consequence of administration of an anti-inflammatory drug or cox-2 inhibitor, particularly an NSAID, steroid, or selective cox-2 inhibitor. Cardiovascular complications are also known as "cardiovascular events". In the following only or mostly the term "cardiovascular complication" will be used.

The term "cardiovasular complication" is known to the person skilled in the art. Thus, a "cardiovascular complication" according to the present invention relates to any kind of such cardiovascular complication or heart failure (particularly acute heart failure) known to the person skilled in the art, particularly the term refers to a complication related to arterial thrombosis or development of arterial thrombosis. Arterial thrombosis may cause coronary syndromes (e.g. acute myocardial infarction or stroke).

Particularly, "cardiovascular complication" relates to a complication in the arterial system, e.g. ACS, UAP, MI, ST-elevated MI, non-ST-elevated MI, or stroke.

More particularly, "cardiovascular complication" relates to MI, ST-elevated MI, non-ST-elevated MI, or stroke.

Symptoms of cardiovascular diseases are known to the person skilled in the art and may include e.g new Q-waves or bundle branch block, signs of non-fatal stroke, the onset or worsening of heart failure as suggested by development of edema or worsening of preexistent edema of the lower extremities, rales on auscultation or pulmonary congestion, new onset of arterial hypertension or worsening of preexistent arterial hypertension, and venous thrombosis.

Symptoms of cardiovascular diseases have been classified into a functional classification system according to the New York Heart Association (NYHA). Patients of Class I have no obvious symptoms of cardiovascular disease. Physical activity is not limited, and ordinary physical activity does not cause undue fatigue, palpitation, or dyspnea (shortness of breath). Patients of class II have slight limitation of physical activity. They are comfortable at rest, but ordinary physical activity results in fatigue, palpitation, or dyspnea. Patients of class III show a marked limitation of physical activity. They are comfortable at rest, but less than ordinary activity causes fatigue, palpitation, or dyspnea. Patients of class IV are unable to carry out any physical activity without discomfort. They show symptoms of cardiac insufficiency at rest. If any physical activity is undertaken, discomfort is increased.

A cardiovascular complication according to the present invention may eventually cause symptoms, particularly symptoms according to NYHA class II-IV, more particularly according to NYHA class III-IV.

Another characteristic of cardiovascular complication or insufficiency can be the "left ventricular ejection fraction" (LVEF) which is also known as "ejection fraction". People with a healthy heart usually have an unimpaired LVEF, which is generally described as above 50%. Most people with a systolic heart disease which is symptomatic generally have an LVEF of 40% or less.

A cardiovascular complication (e.g. MI) may eventually result in an LVEF of 40% or less.

A cardiac insufficiency may either be "compensated" or "decompensated". Compensated means that the regular oxygen need of the body can still be satisfied, whereas decompensated means that the regular oxygen need of the body is not satisfied anymore.

"Diagnosing the cardiovascular risk" according to the present invention includes diagnosing (i.e. becoming aware of) a cardiovascular risk, but also monitoring an elevation or decrease of a pre-existing or known cardiovascular risk.

The term "patient" according to the present invention relates to a healthy individual, an apparently healthy individual, or particularly an individual suffering from a disease. The patient can be both a male or a female individual, as the present invention is suited for diagnosing both groups. Particularly, the patient is suffering from and/or treated for rheumatism, rheumatoid arthritis (chronic polyarthritis), osteoarthritis, psoriatic arthritis, spondyloarthropathy, or other inflammatory diseases or osteoarthrosis. The patient may also be suffering from ulcerations or cancer. In this context it should be noticed that the aforementioned diseases are diseases in which administration of compounds having cox-2 inhibiting properties (as anti-inflammatory drugs), in particular NSAIDs, steroids, or selective cox-2 inhibitors is considered as part of the treatment. Even more particularly, the patient has no known history of cardiovascular risk or complication, and/or no or little symptoms of a cardiovascular risk or complication, and/or he is not being treated for a cardiovascular disease, risk, or complication. However, also healthy individuals who have no signs or history of a cardiovascular risk or complication are considered to be patients according to the present invention.

Preferably, the patient is treated or is about to be treated with an anti-inflammatory drug. Such a patient is understood to be a "candidate" for treatment with said drug. More preferably, the patient is treated or is about to be treated with a selective cox-2 inhibitor. Such a patient is understood to be a "candidate" for treatment with a selective cox-2 inhibitor. Of course, treatment with the respective drug or selective cox-2 inhibitor should in general be considered an advisable treatment option.

It is known to the person skilled in the art, under what circumstances a cardiovascular complication can be considered to occur "as a consequence" of administration of an anti-inflammatory drug or a cox-2 inhibitor, in particular of an NSAID, steroid, or selective cox-2 inhibitor. It should be understood that it may not be possible or necessary to definitively establish the causal relationship. It may be sufficient to establish a sufficiently high probability that the cardiovascular complication was or will be precipitated by administration of the anti-inflammatory drug or cox-2 inhibitor, in particular an NSAID, steroid, or selective cox-2 inhibitor. E.g., the APPROVE study indicates an almost four-fold increase in the number of cardiovascular complications between the test and the placebo group. For the purpose of the present invention, it may be justified to assume that any cardiovascular complication in a patient being treated with a selective cox-2 inhibitor is also caused by the treatment. Thus, the present invention also relates to diagnosing the risk to suffer from a cardiovascular complication after administration of an anti-inflammatory drug, cox-2 inhibitor, NSAID, or selective cox-2 inhibitor.

Furthermore, the person skilled in the art is familiar with methods or signs indicating a causal relationship. For example, a time relationship between administration of the drug and the manifestation of a cardiovascular complication is always an indicator that the drug has been causal for the complication or "precipitated" the complication. E.g. the increase in the number of cardiovascular complications in the APPROVE study became evident after 18 months of treatment. In another example, if the severity of the cardiovascular complication correlates with the amount of the drug administered, it may indicate a causal relationship. For example, pathological changes in an echocardiogram or electrocardiogram may improve upon discontinuing treatment with the drug. In a particular example, the level of one or more cardiac hormones may be monitored before and during administration of the anti-inflammatory drug. If the level of the cardiac hormone increases upon beginning of treatment and decreases upon discontinuing treatment with the drug, it indicates that the drug is causing an elevation of the cardiovascular risk. Similarly, if the level correlates with the dosage of the drug, it also indicates that the drug is causing an elevation of the cardiovascular risk. Any cardiovascular complication manifesting under such circumstances is likely to be caused by the administration of the drug. This is even more likely, if the increase of the level of the cardiac hormone upon administration of the drug is unusually high compared to other patients or if a small increase in dosage causes an unusually steep increase in the level of the cardiac hormone.

Anti-inflammatory drugs are known to the person skilled in the art. Particularly, such drugs include non-steroid anti-rheumatics (also known as non-steroidal anti-inflammatory drugs, NSAIDs), cox-2 inhibitors, corticosteroids, and TNF inhibitors.

Examples for anti-inflammatory drugs include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Celecoxib; Rofecoxib (VIOXX); Etoricoxib; Valdecoxib; Parecoxib; lumiracoxib; Deflazacort; Desonide; Desoximetasone; Dexamethasone Dipropionate; Diclofenac; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluormetholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminium; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Meloxicam (Mobic™); Mesalamine; Meseclazone; Methylprednsisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Soidum; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium; Etanercept; Lenercept; Infliximab; Cortisone; Fluocortolone; Hydrocortisone; Methyl-prednisolone; Prednisolone; Prednisone; Prednylidene.

As the case may be, it is comprised in the present invention to measure the cardiac hormone or natriuretic peptide, e.g. NT-proBNP, also before administering any of the above-mentioned compounds.

The term "non-steroidal anti-rheumatics" (also referred to as non-steroidal anti-inflammatory drugs or NSAIDs) is known to the person skilled in the art. NSAIDs inhibit cyclooxygenases (also known as prostaglandin-H-synthetases). Cyclooxygenases catalyze the reaction from arachidonic acid to prostaglandin $H_2$ (a cyclic endoperoxide), which is the precursor of prostaglandin $I_2$ (also known as prostacycline), thromboxan $A_2$, and other prostaglandins. Prostaglandins play a significant role in pain, fever, and inflammatory reactions. There are two isoforms of cyclooxygenases, Cox-1 and cox-2. The cox-2 gene is an immediate early gene and is induced under conditions of tissue damage, pain reactions, or inflammatory reactions. Thus, NSAIDs include Cox-1 inhibitors and cox-2 inhibitors. The NSAIDs may inhibit both isoforms or they may be selective for one isoform (i.e. they inhibit only one of the two isoforms at the therapeutic dosage).

Examples for unspecific NSAIDs include Ibuprofen; Flurbiprofen; Naproxen; Flufenamic Acid; Mefenamic Acid; Piroxicam; Diclofenac; Phenbutazone Sodium Glycerate; Indometacin; Tenoxicam.

Selective cox-2 inhibitors according to the present invention are compounds which, under therapeutic conditions, do inhibit expression or, preferably, the enzymatic function of cox-2, whereas not significantly inhibiting expression or, preferably, the enzymatic function of Cox-1. Examples for selective cox-2 inhibitors include coxibes (e.g. celecoxib, rofecoxib, etoricoxib, valdecoxib, parecoxib (a pro-drug of valdecoxib), lumiracoxib), meclofenatmate, sulindac sulphide, diclofenac, nimesulide, meloxicam, etodolac, NS398, L-745,337, DFP (3-(2-propyloxy)-4-(4-methylsulphonylphenyl)-5,5-dimethylfuranone). The latter three compounds are described in Warner, T. D., et al., 1999.

The enzymatic function of the two cyclooxygenases can be measured according to methods known in the art, including suitable in vivo or in vitro tests. A typical marker for the enzymatic function of Cox-1 is the formation of thromboxan $A_2$, whereas a typical marker for the enzymatic function of cox-2 is the formation of prostaglandins (e.g. prostaglandin $E_2$ from macrophages.

Examples for a suitable test systems have been published (e.g. Warner, T. D., Giuliano, F., Vojnovic, I., et al. (1999). Nonsteroid drug selectivities for cyclo-oxygenase-1 rather than cyclo-oxygenase-2 are associated with human gastrointestinal toxicity: A full in vitro analysis. Proceedings of the National Academy of Sciences USA, vol. 96., pp. 7563-7568, a relevant erratum has been published in vol. 96(17), p. 9966d). This assay will be referred to as the William Harvey Modified Assay. The assay is described in detail in Warner T. D., et al. supra, on page 7563-4, the description of which is expressly incorporated herein by reference.

Figure 3:
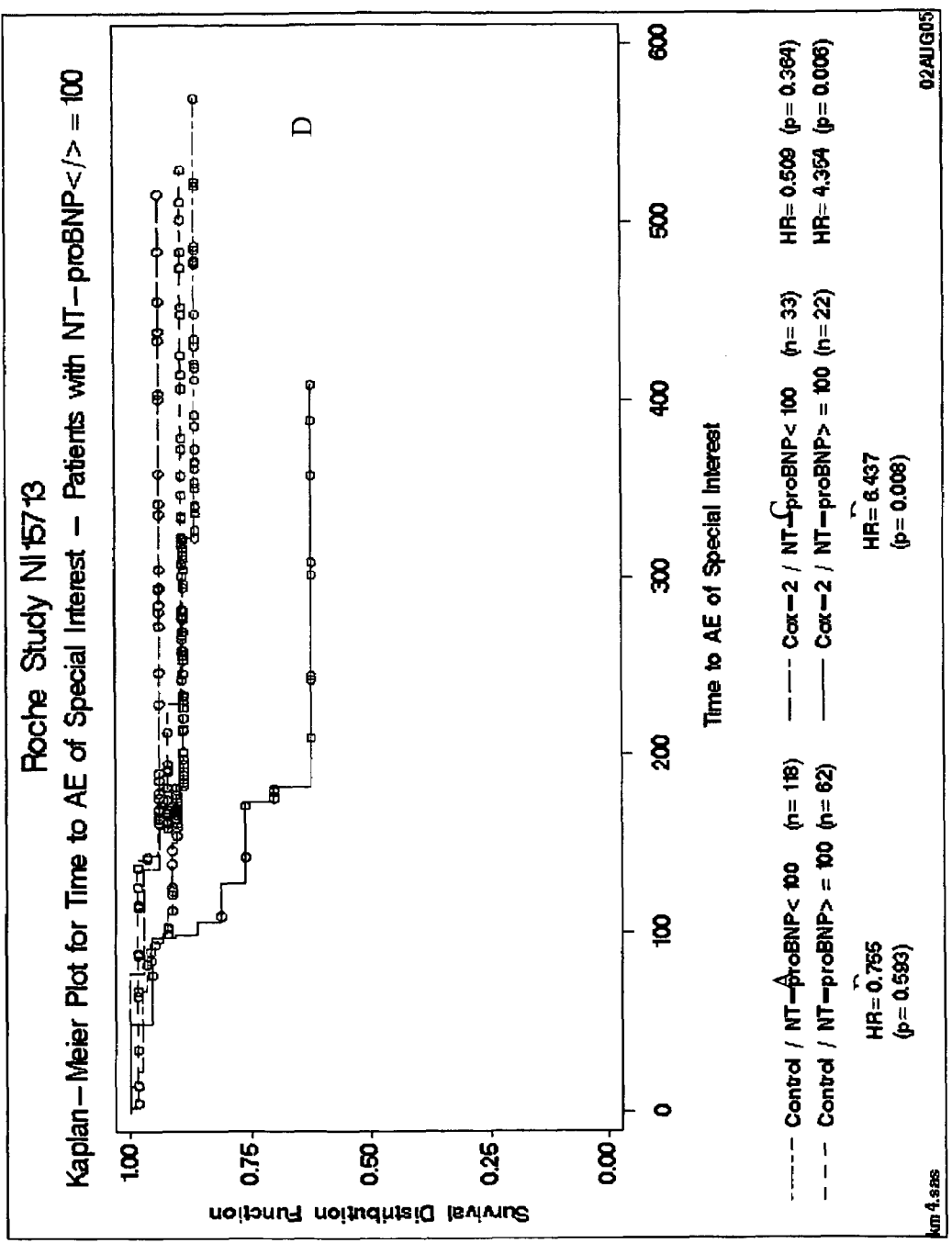
FIG. 3: This figure refers to Example 5. Kaplan-Meier curve based on cardiologist adjudicated cardiovascular adverse events (CV-AEs) for cox-2 inhibitors group and comparison group with NT-proBNP<100 pg/ml vs. NT-proBNP>100 pg/ml. In the light of findings demonstrating an excess risk for CV-AEs with selective inhibition of cox-2, the crude CV-AEs were reconciled by cardiologist blinded to the NT-proBNP values using prespecified definition criteria. Plotting these adjudicated CV-AEs over time as Kaplan-Meier curve demonstrates a 4.4-fold higher risk in the cox-2 inhibitors group with NT-proBNP>100 pg/ml compared with the comparison group (control) and a 6.4-fold higher risk compared with the cox-2 inhibitors group with NT-proBNP<100 pg/ml. This risk was almost completely restricted to patients with an NT-proBNP>100 pg/ml on study entry or at 24 weeks of follow-up. Hazard ratios at the right indicate the hazard ratios for the groups compared indicated to the left (control vs. cox-2 inhibitors group), whereas hazard ratios given at the bottom of the figure refer to the groups compared above (NT-proBNP levels of less than 100 pg/ml vs. NT-proBNP levels of 100 pg/ml or higher). AE, adverse event; n, number; HR, hazard ratio; p, probability; survival distribution function, event-free survival distribution function.

Preferably, a selective cox-2 inhibitor according to the present invention is more than 5-fold cox-2 selective according to the William Harvey Modified Assay, more preferably more than 50-fold cox-2 selective according to the William Harvey Modified Assay (see Warner, T. D. et al., supra, FIG. 3 on page 7567).

Alternatively, the selective cox-2 inhibitor according to the present invention is a compound preferably being more selective for cox-2 than diclofenac, more preferably being more selective for cox-2 than nimesulide, even more preferably at least as selective as for cox-2 as celecoxib under therapeutic conditions.

In another preferred embodiment, the present invention relates to means and methods for diagnosing the cardiovascular risk of a patient who is a candidate for administration of a "coxibe". Examples for coxibes include celecoxib (Celebrex™, Pfizer), rofecoxib (VIOXX™, Merck), etoricoxib, valdecoxib, parecoxib (a pro-drug of valdecoxib), lumiracoxib (Prexige™, Novartis). Other similar compounds, several of which are under development and examination, are also included in the scope of the present invention.

The currently discussed pathomechanism for the undesired cardiovascular side-effects of selective cox-2 inhibitors may be as follows: The inhibition of prostaglandin $I_2$ ($PGI_2$) formation is attributed a major role in the genesis of these cardiovascular incidents. $PGI_2$ leads to inhibition of thrombocyte aggregation, vasodilatation and prevention of the proliferation of smooth muscle cells in vitro.

On the other hand, thromboxane $A_2$, the most important COX-1 product of platelets leads to platelet aggregation, vasoconstriction and vascular proliferation. It is suspected that the interference with the balanced equilibrium between $PGI_2$ and thromboxane $A_2$ promotes intravascular activation of hemostasis, leads to an increase in blood pressure and enhances the acceleration of atherosclerosis.

Thus, in a preferred embodiment, the present invention also relates to the use of cardiac hormones for assessing the cardiovascular risk of a patient with respect to the administration of an anti-inflammatory drug wherein the cardiovascular risk is caused by a disturbance of the balanced equilibrium between Cox-1 and cox-2 inhibition, and/or the prostaglandin metabolism and/or the balanced equilibrium between $PGI_2$ and thromboxane $A_2$, more particularly the inhibition of the $PGI_2$ formation. The present invention also relates to the use of cardiac hormones for assessing the cardiovascular risk of a patient with respect to the administration of an anti-inflammatory drug which promotes intravascular thrombosis, and/or leads to an increase in blood pressure and/or enhances the acceleration of atherosclerosis. Most preferably, the present invention does not relate to the use of cardiac hormones for assessing the risk of suffering from a cardiovascular complication wherein the risk is due to an increase of blood volume or intravasal volume (volume overload).

In the present context, the term "steroid" is used as an abbreviation of the term "corticosteroid". It is generally thought that corticosteroids exert their anti-inflammatory activity by influencing the prostaglandin metabolism. Examples for corticosteroids according to the present invention include cortisone; fluocortolone; hydrocortisone; methyl-prednisolone; prednisolone; prednisone; prednylidene.

TNF inhibitors are also used as anti-inflammatory drugs, in particular in patients with rheumatoid arthritis (increased concentrations of TNF-α were found in patients suffering from rheumatoid arthritis). Inhibition of TNF-α also reduces the formation of IL-1 and IL-6. Examples for TNF inhibitors include Etanercept, Lenercept (an analogon of Etanercept), Infliximab, and D2E7 (a completely humanized monoclonal antibody against TNF-α).

In another preferred embodiment, the present invention relates to additionally measuring the level of at least one marker chosen from the group consisting of (a) markers of inflammation, (b) markers of endothel function, (c) markers of ischemia, (d) markers of thrombocyte activation, (e) markers of atherosclerosis activation, and (f) markers of intravascular activation of coagulation.

Measuring an additional marker may increase the selectivity and specificity of diagnosis. It may also serve to confirm a diagnosis established by measuring the level of a natriuretic peptide.

Markers of inflammation according to the present invention include any markers indicative of an inflammatory process, particularly a vascular or arterial inflammatory process. Particularly, markers of inflammation according to the present invention comprise inflammatory active cytokines. Examples for markers of inflammation include interferons (e.g. interferon gamma), interleukins (e.g. IL-1, IL-6, IL-8), Tumor necrosis factor (TNF) alpha), CRP (C-reactive protein), hsCRP (high-sensitivity C-reactive protein).

Markers of endothel function according to the present invention comprise any markers indicative of intravascular repair processes, including cytokines related to such processes. Examples for such markers include selectins (e.g. E-selectin, P-selectin), ICAM-1 (intercellular cell adhesion molecule-1), VCAM-1 (vascular cell adhesion molecule-1), PDGF (platelet-derived growth factor), TGF-alpha, TGF-beta, catecholamines, prostaglandins, angiotensin, endothelin, NO (nitric oxide). Although already mentioned as being markers of inflammation, TNF-alpha, TNF-beta, and IL-1 may also be considered to belong to the group of markers of endothel function.

Markers of ischemia according to the present invention comprise any markers indicative of insufficient oxygen supply resulting in ischemia. Particularly, the insufficient oxygen supply is local and any resulting ischemia is also local. Such local ischemia may be caused by arterial thrombosis limiting the blood flow to the target tissue of the affected artery. Examples for markers of ischemia include ischemic modified albumin (IMA) and high- sensitive troponins (e.g. TnI and TnT).

Markers of thrombocyte activation according to the present invention comprise any markers indicative of activation or aggregability of blood platelets. A preferred marker is soluble CD40 ligand (sCD40L). It should be understood that thrombocyte activation or platelet aggregability may also be measured by analysis of a thrombocyte-rich blood plasma sample. After taking the sample, a trigger substance is added and the time-course of aggregation of thrombocytes is measured by the reduction in turbidity. The reduction in turbidity is caused by the aggregation of the many small platelets into larger aggregates, which reduces the light scatter. The trigger substance may be any substance deemed appropriate by the person skilled in the art (e.g. adenosine diphosphate (ADP), serotonin, collagen, protease, or ristocetine). Diagnosis can be performed by comparing the result of the measurement to result of the same experiment in a control sample or control group. Therefore, such test may be considered a marker according to the present invention.

Markers of atherosclerosis activation according to the present invention comprise any markers indicative of progression of atherosclerosis. Examples for markers of atherosclerosis activation include lipoprotein-associated phospholipase A2 (Lp-PLA2).

Examples for markers of intravascular activation of coagulation include fibrinogen degradation products, D-dimer, plasminogen activator inhibitor.

Diagnosis according to the present invention is preferably done by use of a diagnostic means. A diagnostic means is any means that allows to measure the level amount, or concentration of a substance of interest, particularly a peptide or polypeptide of interest, more particularly a cardiac hormone.

Methods and diagnostic means which can be used to determine the levels of the respective peptides are known to the person skilled in the art. These methods include microplate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

Furthermore, the person skilled in the art is familiar with different methods of measuring the level of a peptide or polypeptide. The term "level" relates to amount or concentration of a peptide or polypeptide in a patient (more specifically, in the blood or urine of the patient), or a sample taken from a patient (e.g. a blood or urine sample). The term "measuring" according to the present invention relates to determining the amount or concentration, preferably semi-quantitatively or quantitatively, of the nucleic acid, peptide, polypeptide, or other substance of interest. Measuring can be done directly or indirectly. Indirect measuring includes measuring of cellular responses, bound ligands, labels, or enzymatic reaction products.

In the context of the present invention, amount also relates to concentration. It is evident, that from the total amount of a substance of interest in a sample of known size, the concentration of the substance can be calculated, and vice versa.

Measuring can be done according to any method known in the art. Preferred methods are described in the following.

In one embodiment, the method for measuring the level of a peptide or polypeptide of interest, particularly a cardiac hormone, comprises the steps of (a) contacting a cell capable of a cellular response to the peptide or polypeptide with the peptide or polypeptide for an adequate period of time, (b) measuring the cellular response.

In another embodiment, the method for measuring the level of a peptide or polypeptide of interest, particularly a cardiac hormone, comprises the steps of (a) contacting a peptide or polypeptide with a suitable substrate for an adequate period of time, (b) measuring the amount of product.

In another embodiment, the method for measuring the level of a peptide or polypeptide of interest, particularly a cardiac hormone, comprises the steps of (a) contacting a peptide or polypeptide with a specifically binding ligand, (b) (optionally) removing non-bound ligand, (c) measuring the amount of bound ligand.

Preferably, the peptide or polypeptide is contained in a sample, particularly a body fluid or tissue sample, and the amount of the peptide or polypeptide in the sample is measured.

Peptides and polypeptides (proteins) can be measured in tissue, cell, and body fluid samples, i.e. preferably in vitro. Preferably, the peptide or polypeptide of interest is measured in a body fluid sample.

A tissue sample according to the present invention refers to any kind of tissue obtained from the dead or alive human or animal body. Tissue samples can be obtained by any method known to the person skilled in the art, for example by biopsy or curettage.

Body fluids according to the present invention may include blood, blood serum, blood plasma, lymphe, cerebral liquor, saliva, and urine. Particularly, body fluids include blood, blood serum, blood plasma, and urine. Samples of body fluids can be obtained by any method known in the art.

Methods to obtain cell samples include directly preparing single cells or small cell groups, dissociating tissue (e.g. using trypsin), and separating cells from body fluids, e.g. by filtration or centrifugation. Cells according to the present invention comprise also platelets and other non-nuclear cells, e.g. erythrocytes.

If necessary, the samples may be further processed. Particularly, nucleic acids, peptides or polypeptides may be purified from the sample according to methods known in the art, including filtration, centrifugation, or extraction methods such as chloroform/phenol extraction.

For measuring cellular responses, the sample or processed sample is added to a cell culture and an internal or external cellular response is measured. The cellular response may include the expression of a reporter gene or the secretion of a substance, e.g. a peptide, polypeptide, or a small molecule.

Other preferred methods for measurement may include measuring the amount of a ligand binding specifically to the peptide or polypeptide of interest. Binding according to the present invention includes both covalent and non-covalent binding.

A ligand according to the present invention can be any peptide, polypeptide, nucleic acid, or other substance binding to the peptide or polypeptide of interest. It is well known that peptides or polypeptides, if obtained or purified from the human or animal body, can be modified, e.g. by glycosylation. A suitable ligand according to the present invention may bind the peptide or polypeptide also via such sites.

Preferably, the ligand should bind specifically to the peptide or polypeptide to be measured. "Specific binding" according to the present invention means that the ligand should not bind substantially to ("cross-react" with) another peptide, polypeptide or substance present in the sample investigated. Preferably, the specifically bound protein or isoform should be bound with at least 3 times higher, more preferably at least 10 times higher and even more preferably at least 50 times higher affinity than any other relevant peptide or polypeptide.

Non-specific binding may be tolerable, particularly if the investigated peptide or polypeptide can still be distinguished and measured unequivocally, e.g. according to its size on a Western Blot, or by its relatively higher abundance in the sample.

Binding of the ligand can be measured by any method known in the art. Preferably, the method is semi-quantitative or quantitative. Suitable methods are described in the following.

First, binding of a ligand may be measured directly, e.g. by NMR or surface plasmon resonance.

Second, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot).

For measurement of enzymatic reaction products, preferably the amount of substrate is saturating. The substrate may also be labeled with an detectable label prior to the reaction. Preferably, the sample is contacted with the substrate for an adequate period of time. An adequate period of time refers to the time necessary for an detectable, preferably measurable amount of product to be produced. Instead of measuring the amount of product, the time necessary for appearance of a given (e.g. detectable) amount of product can be measured.

Third, the ligand may be coupled covalently or non-covalently to a label allowing detection and measurement of the ligand.

Labelling may be done by direct or indirect methods. Direct labelling involves coupling of the label directly (covalently or non-covalently) to the ligand. Indirect labelling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.)

The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus.

Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels.

Enzymatically active labels include e.g. horseradish peroxidase, alkaline phosphatase, beta-Galactosidase, Luciferase, and derivatives thereof. Suitable substrates for detection include diamino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemoluminescence, which can be measured according to methods known in the art (e.g. using a light-sensitive film or a suitable camera system). As for measuring the enyzmatic reaction, the criteria given above apply analogously.

Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molcular Probes (Oregon). Also the use of quantum dots as fluorescent labels is contemplated.

Typical radioactive labels include $^{35}$S, $^{125}$I, $^{32}$P, $^{33}$P and the like. A radioactive label can be detected by any method known and appropriate, e.g. a light-sensitive film or a phosphor imager.

Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoroimmunoassay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labeling or other detection methods as described above.

Preferred ligands include antibodies, nucleic acids, peptides or polypeptides, and aptamers, e.g. nucleic acid or peptide aptamers. Methods to such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display.

The term "antibody" as used herein includes both polyclonal and monoclonal antibodies, as well as fragments thereof, such as Fv, Fab and F(ab)$_2$ fragments that are capable of binding antigen or hapten. The present invention also includes "humanized" hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art.

In another preferred embodiment, the ligand, preferably chosen from the group consisting of nucleic acids, peptides, polypeptides, more preferably from the group consisting of nucleic acids, antibodies, or aptamers, is present on an array.

Said array contains at least one additional ligand, which may be directed against a peptide, polypeptide or a nucleic acid of interest. Said additional ligand may also be directed against a peptide, polypeptide or a nucleic acid of no particular interest in the context of the present invention. Preferably, ligands for at least three, preferably at least five, more preferably at least eight peptides or polypeptides of interest in the context of the present invention are contained on the array.

According to the present invention, the term "array" refers to a solid-phase or gel-like carrier upon which at least two compounds are attached or bound in one-, two- or three-dimensional arrangement. Such arrays (including "gene chips", "protein chips", antibody arrays and the like) are generally known to the person skilled in the art and typically generated on glass microscope slides, specially coated glass slides such as polycation-, nitrocellulose- or biotin-coated slides, cover slips, and membranes such as, for example, membranes based on nitrocellulose or nylon.

The array may include a bound ligand or at least two cells expressing each at least one ligand.

It is also contemplated to use "suspension arrays" as arrays according to the present invention (Nolan J P, Sklar L A. (2002). Suspension array technology: evolution of the flat-array paradigm. Trends Biotechnol. 20(1):9-12). In such suspension arrays, the carrier, e.g. a microbead or microsphere, is present in suspension. The array consists of different microbeads or microspheres, possibly labelled, carrying different ligands.

The invention further relates to a method of producing arrays as defined above, wherein at least one ligand is bound to the carrier material in addition to other ligands.

Methods of producing such arrays, for example based on solid-phase chemistry and photo-labile protective groups, are generally known (U.S. Pat. No. 5,744,305). Such arrays can also be brought into contact with substances or substance libraries and tested for interaction, for example for binding or change of confirmation. Therefore, arrays comprising a peptide or polypeptide as defined above may be used for identifying ligands binding specifically to said peptides or polypeptides.

Furthermore, it is contemplated to use so called point-of-care or lab-on-a-chip devices for obtaining the sample and measurement of the marker. Such devices may be designed analogously to the devices used in blood glucose measurement. Thus, a patient will be able to obtain the sample and measure the marker without immediate assistance of a trained physician or nurse.

Means suitable for measuring the expression level of a marker according to the present invention, such as antibodies, aptamers, antisense nucleic acids etc. have been already been described in detail earlier in this specification. In a preferred embodiment, the means is packed as a kit comprising a container for the means or agent for measurement as well as containers for any auxiliary agents for measurement, e.g. suitable buffers, filters, columns, enyzmes, etc.

In another preferred embodiment, it is contemplated that the means is a lab-on-a-chip device or any other device suitable for point-of-care diagnosis. Devices for point-of-care diagnosis are known in the art. Preferably, such a device comprises a sampling unit (e.g. for taking a blood sample) and a measurement unit (e.g. for measuring the binding of the marker to a ligand). The means may also be a test strip or other auxiliary tool for measuring the expression level of the marker in such a device.

Therefore, in another embodiment, the present invention also relates to a kit, a lab-on-chip device, or a point-of-care diagnostic device for measuring the expression level of the marker.

The method according to the present invention comprises the step of diagnosing the risk of the patient by comparing the measured level to known levels associated with different grades of risk in a patient.

The person skilled in the art is able to determine known levels of cardiac hormones which are associated with different grades of cardiovascular risk with respect to administration of an anti-inflammatory drug, particularly an NSAID, steroid, or selective cox-2 inhibitor. In general, the higher the level of the cardiac hormone, the higher is the risk for the patient.

According to the present invention, the term "risk" relates to the probability of a particular incident, more particularly a cardiovascular complication, to take place. The grade of risk can be increased or highly increased. The grade of risk can also not be increased. "No increased risk" means that there is apparently no risk of a cardiovascular event with respect to administration of an anti-inflammatory drug, particularly an NSAID, steroid, or selective cox-2 inhibitor.

Guidance as to what levels are associated with which grade of risk can be drawn from levels of cardiac hormones known to be associated with the presence or severity of a cardiovascular disease. For example, based on a 97.5 percentile obtained in individuals below the age of 50, a plasma level of 125 pg/ml of NT-proBNP may be considered a normal level (more specifically, an NT-proBNP plasma level of 100 pg/ml for males and 150 pg/ml for females may be considered a normal level). Higher levels of NT-proBNP correlate for example with the level of symptoms according to the NYHA classification and with the level of impairment of LVEF. The term "plasma level" relates to levels of NT-proBNP measured in blood plasma. The levels measured in plasma are generally comparable to the levels measured in blood serum.

In another example, based on a 97.5 percentile obtained in apparently healthy individuals below the age of 65, a plasma levels of less than 84 pg/ml for men and less than 155 pg/ml for females of NT-proBNP may be considered as levels indicating no increased risk. In patients complaining of dyspnea levels of less than 100 pg/ml for men and less than 150 pg/ml for females may be considered as exclusion criteria for heart failure or ventricular dysfunction. Higher levels of NT-proBNP than the levels mentioned in this example correlate for example with the level of symptoms according to the NYHA classification and with the level of impairment of LVEF. The term "plasma level" relates to levels of NT-proBNP measured in blood plasma. Again, the levels measured in plasma and blood serum are generally comparable.

Below, plasma levels of NT-proBNP are given which are or can be typically considered to be associated with the indicated grades of cardiovascular risk with respect to administration of an anti-inflammatory drug, a cox-2 inhibiting compound, particularly an NSAID, steroid, or selective cox-2 inhibitor.

It is evident, that the levels given below can serve only as a first classification of the risk of a patient. The person skilled in the art is able to determine other relevant levels from the literature (e.g. Wang, T. J., Larson, M. G., Levy, D., et al. (2004) Plasma natriuretic peptide levels and the risk of cardiovascular events and death. N Engl J Med, vol. 350, pp.

655-63; Olson, M. H., Wachtell, K. Tuxen, C., Fossum, E. et al. (2004) N-terminal pro-brain natriuretic peptide predicts cardiovascular events in patients with hypertension and left hypertrophy: a LIFE study. J Hypertens, vol. 22, pp. 1597-1604) or from other clinical studies.

Typically, a plasma level of less than 125 pg/ml of NT-proBNP is associated with no increased cardiovascular risk with respect to administration of an anti-inflammatory drug, a cox-2 inhibitor, particularly an NSAID, steroid, or selective cox-2 inhibitor.

Typically, a plasma level from 125 to 500 pg/ml of NT-proBNP is associated with an increased cardiovascular risk with respect to administration of an anti-inflammatory drug, a cox-2 inhibitor, particularly an NSAID, steroid, or selective cox-2 inhibitor. However, also a level between 80 and 125 pg/ml should warrant further clarification of whether an increased risk is present.

Typically, a plasma level more than 500 pg/ml of NT-proBNP is associated with a highly increased cardiovascular risk with respect to administration of an anti-inflammatory drug, a cox-2 inhibitor, particularly an NSAID, steroid, or selective cox-2 inhibitor. However, also a level of more than 400 pg/ml should warrant further clarification of whether a highly increased risk is present.

Once the risk in a patient has been diagnosed, it may have consequences for the subsequent treatment as described below (a non-limiting example for such treatment decisions is also given in FIG. 1). The grades of risk mentioned below particularly refer to the grades of risk associated with the above described levels of NT-proBNP.

If a method according to the present invention indicates no increased risk, then the anti-inflammatory drug may be administered, preferably taking into account any other known risk factors for cardiovascular disease. Preferably, administration of the drug is accompanied by further monitoring of the level of the cardiac hormone, particularly in case of high dosage or long-term application of the drug. Thus, it will be possible to early detect any unusual increase in the level of the cardiac hormone which would indicate an elevation of the cardiovascular risk.

If a method according to the present invention indicates an increased risk, then the patient is preferably investigated intensively by further diagnosis according to methods known to the skilled cardiologist, such as electrocardiography, echocardiography. Treatment with a an anti-inflammatory drug, most particularly a selective cox-2 inhibitor, should only be initiated upon careful consideration of risk and potential benefit. Notably, the present invention will not only help to make the administration of anti-inflammatory drugs safer by identifying risk patients, but it may also help to uncover a previously unnoticed cardiovascular risk in a patient. Thus, a patient having an increased or highly increased cardiovascular risk is preferably subjected to further diagnosis to identify an underlying cardiovascular disorder. This will allow initiating treatment early, i.e. before the onset of obvious symptoms of the cardiovascular disorder. Thus, the general health of the patient will profit from the present invention's methods to diagnose the cardiovascular risk before or during administration of an anti-inflammatory drug. Furthermore, if treatment of the underlying cardiovascular disorder is successful, the risk may be reduced (as diagnosed according to the means and methods provided by the present invention) and treatment with an anti-inflammatory drug, particularly an NSAID, steroid, or selective cox-2 inhibitor can be initiated or the dosage of such drug can be increased.

Treatment of a patient having an increased risk may also be accompanied by further measures such as limiting or reducing the dosage of an anti-inflammatory drug administered or about to be administered, restriction of salt intake, regular moderate exercise, providing influenzal and pneumococcal immunization, surgical treatment (e.g. revascularization, balloon dilatation, stenting, by-pass surgery), administering drugs such as diuretics (including co-administration of more than one diuretic), ACE (angiotensin converting enzyme) inhibitors, β-adrenergic blockers, aldosterone antagonists, calcium antagonists (e.g. calcium channel blockers), angiotensin-receptor blockers, digitalis and any other measures known and deemed appropriate by the person skilled in the art.

The present invention also comprises a method of monitoring the treatment with a cox-2 inhibiting compound, particularly an NSAID, steroid, or selective cox-2 inhibitor, wherein the level of a cardiac hormone, in particular NT-proBNP, is measured.

If, based upon consideration of risk and potential benefit, treatment with a cox-2 inhibiting compound, in particular with an NSAID, steroid, or selective cox-2 inhibitor is initiated, it may also be as an intermittent therapy. Measuring a natriuretic peptide may then be used to monitor therapy, particularly intermittent therapy, and/or to identify an elevation of the risk. The administration is stopped when the level of cardiac hormone reaches a certain value and is optionally re-initiated when the level falls below a certain value. The respective values of the cardiac hormone are those mentioned beforehand. For example, a value indicating to stop administration may be a value which normally would indicate a highly increased risk (as described elsewhere in this specification). Then, a value indicating to optionally re-initiate treatment may be a value indicating merely an increased risk (as described elsewhere in this specification) or a value indicating no increased risk (as described elsewhere in this specification).

From the above it is evident that the present invention also provides a method of monitoring of a patient who is being treated or who is about to be treated with a cox-2 inhibiting compound, in particular an NSAID, steroid, or a selective cox-2 inhibitor.

If a method according to the present invention indicates a highly increased risk, then treatment may be adapted as described for increased risk. However, administration of a cox-2 inhibiting compound, in particular an NSAID, steroid, or a selective cox-2 inhibitor, will a priori not be a treatment option for a patient with a highly increased risk. If, for whatever the reason may be, a cox-2 inhibiting compound, in particular an NSAID, or steroid, most particularly a selective cox-2 inhibitor, is administered, it should only be done under careful medical supervision, in particular including measuring of a natriuretic peptide at short intervals to monitor the risk and/or to identify an elevation of the risk.

SPECIFIC EMBODIMENTS

The following examples illustrate the invention and are not intended to limit its scope in any way.

EXAMPLE 1

Measurement of NT-proBNP

NT-proBNP can be determined by an electrochemoluminescence immunoassay (Elecsys proBNP sandwich immuno assay; Roche Diagnostics, Mannheim, Germany) on Elecsys 2010. The assay works according to the electrochemoluminescence sandwich immunoassay principle. In a first step, the biotin-labelled IgG (1-21) capture antibody, the ruthenium-labelled F(ab')$_2$ (39-50) signal antibody and 20 microliters of sample are incubated at 37° C. for 9 minutes. Afterwards, streptavidin-coated magnetic microparticles are added and the mixture is incubated for additional 9 minutes. After the second incubation, the reaction mixture is transferred to the measuring cell of the system where the beats are magnetically captured onto the surface of an electrode. Unbound label is removed by washing the measuring cell with buffer.

In the last step, voltage is applied to the electrode in the presence of a tri-propylamine containing buffer and the resulting electrochemoluminescent signal is recorded by a photomultiplier. All reagents and samples are handled fully automatically by the Elecsys™ instrument. Results are determined via a calibration curve which is instrument-specifically generated by 2-point calibration and a master curve provided via the reagent barcode. The test is performed according to the instructions of the manufacturer.

Blood for hormone analysis may be sampled in EDTA-tubes containing 5000 U aprotinine (Trasylol, Bayer, Germany) and Lithium-Heparin-tubes (for clinical chemistry), as appropriate. Blood and urine samples are immediately spun for 10 min. at 3400 rpm at 4° C. Supernatants are stored at −80° C. until analysis.

Measurement of NT-proANP

NT-proANP can be determined by a competitive-binding radioimmuno assay with magnetic solid phase technique in a modification of Sundsfjord, J. A., Thibault, G., et al. (1988). Idenfication and plasma concentrations of the N-terminal fragment of proatrial natriuretic factor in man. J Clin Endocrinol Metab 66:605-10., using the same rabbit-anti-rat proANP polyclonal serum, human proANP (1-30) from Peninsula Lab (Bachem Ltd, St. Helene, UK) as the standard, and iodined, proANP 1-30 purified by HPLC for radio labelling. In order to achieve high sensitivity and good precision, Dynabeads M280 with sheep-anti-rabbit IgG (Dynal Biotech, Oslo, Norway) as solid phase and second antibody may be used.

EXAMPLE 2

A 70-year-old patient suffers from severe rheumatoid arthritis and has received long-term treatment with ibuprofen. During the ibuprufen treatment he has suffered from gastrointestinal side-effects including gastrointestinal bleeds. The physician considers to change treatment to the use of selective cox-2 inhibitors and performs a measurement of NT-proBNP. The NT-proBNP level is 223 pg/ml. The patient is referred to a cardiologist for further diagnosis. By means of echocardiogram, the cardiologist diagnoses an ischemic function defect and a risk for therapy with selective cox-2 inhibitors. Since the cardiac function defect is not severe, an intermittent therapy with a selective cox-2 inhibitor is initiated under close monitoring of NT-proBNP.

EXAMPLE 3

A 55-year-old female patient has been treated for 6 years for diabetes type II and is suffering from a chronic painful rheumatic disease. Therefore, her physician considers treatment with cox-2 inhibitors. The NT-proBNP value is measured and determined to be 647 pg/ml. The patient is referred to a cardiologist for further diagnosis. Due to the high NT-proBNP value and due to the co-morbidity of diabetes, treatment with cox-2 inhibitors is not initiated.

EXAMPLE 4

A 72-year-old patient healthy and smoker, but having no further traditional risk factors for heart disease, suffers from strong joint pain in the knees (probably due to long-time sport activities). The patient knows that his stomach is very sensitive. Therefore, treatment with selective cox-2 inhibitors is considered. The measured plasma NT-proBNP value is determined to be 65 pg/ml. As the PROCAM score is below 40 and the only traditional risk factor is smoking, treatment with selective cox-2 inhibitors is initiated.

EXAMPLE 5

The use of NT-proBNP for assessing the risk of suffering from a cardiovascular complication with respect to the administration of anti-inflammatory drugs.

Importantly, in the context of the present example, the term "cox-2 inhibitor" should be understood as referring to a "selective cox-2 inhibitor". Furthermore, in the context of the present example, the term "NSAID" refers to an NSAID not being a selective cox-2 inhibitor.

NT-proBNP was measured in baseline serum samples from 433 patients entering a prospective study, designed primarily to define the therapeutic effect of a novel metallo-proteinase inhibitor in osteoarthritis (OA). Cardiovascular adverse events (CV-AEs) were monitored and related to the concomitant use of cox-2 inhibitors or NSAIDs or prostaglandin metabolism influencing steroids. In a retrospective analysis the question was evaluated whether CV AEs in patients receiving anti-inflammatory drugs could have been predicted from elevated NT-proBNP values.

The study was originally designed by Hoffmann-La Roche Inc., Basel, Switzerland, to investigate the effect of a novel matrix-metalloprotease (MMP) inhibitor on the progression of primary osteoarthritis (OA) in a dose ranging 24 week trial of the MMP inhibitor Ro 113-0830 in patients with primary knee OA with or without hand OA followed by a 30 months extension. Diagnosis of OA was based on clinical and radiographic criteria. Patients with secondary causes of OA such as inflammatory arthritis, congenital dysplasias and malformation, metabolic and crystal diseases, neuropathy, osteonecrosis, previous articular fracture, Paget's disease of bone, ochronosis, acromegaly, hemochromatosis, Wilson's disease, gout, primary osteochondromatosis were not included. Other exclusion criteria encompassed a history of significant active gastrointestinal (e.g.; erosions, ulcers, bleeding) or renal disease pathology (e.g.; increased creatinine>2.0 mg/dl, renal insufficiency) within 1 year of the screening visit. The study was performed based on a double-blind, randomized, 5‡-arm, placebo controlled, parallel group, multi-center design and dose ranging trial of 24 weeks duration. At the end of the double-blind period patients may have the option to continue in a 30-month extension period with Ro 113-0830 treatment. All patients gave their informed consent. Rescue analgesics (i.e. analgesics deemed necessary as treatment by the responsible physician) and anti-inflammatory drugs including cox-2 inhibitors, NSAIDs or steroids as concomitant therapies were permitted and could be used on an as needed basis by the patient.

Permitted rescue anti-inflammatory drugs including cox-2 inhibitors and NSAIDs or steroids for this trial were aspirin, diclofenac sodium, diflunisal, etodolac, fenoprofen, ibuprofen, ketoprofen, naproxen, nabumetone, oxaprozin, piroxicam, sodium salicylate, choline magnesium salicylate, celecoxib, rofecoxib or tolmetin. The entire study cohort was followed for the occurrence of CV-AEs (cardiovascular adverse events). Patients were not enquired actively for the occurrence of angina pectoris, signs or symptoms of congestive heart failure, or arterial hypertension, nor was the ECG routinely evaluated for the occurrence of new Q-waves or new bundle branch block. All CV-AEs were classified retrospectively by professional external study monitors into different categories.

All CV-AEs were examined by two cardiologists who were not primarily involved in this trial and were blinded to biomarker results. Definite or potentially qualifying CV adverse events encompassed a recording of acute myocardial infarction, new Q-waves or bundle branch block, death from myocardial infarction or other cardiovascular reasons, non-fatal stroke, the onset or worsening of heart failure as suggested by development of edema or worsening of preexistent edema of the lower extremities, rales on auscultation or documented pulmonary congestion on fluoroscopy, new onset of arterial hypertension or worsening of preexistent arterial hypertension, confirmed venous thrombosis. Other ECG signs, unilateral edema or isolated edema of the upper extremities were not regarded as qualifying events.

On each sampling day two 10 mL venous blood samples were collected into separate plain glass tubes, centrifuged and stored at −70° C. or below in polystyrene storage racks. Samples were shipped from the study centres to the Central Sample Office at regular intervals. NT-proBNP was measured using a commercially available sandwich immunoassay on a fully automated analyzer (ELECSYS proBNP, Roche Diagnostics, Mannheim, Germany).

A total of 433 patients with OA were enrolled and received either placebo or the study medication at incremental doses from 10 to 150 mg. The patients were divided according to their co-medication into the following groups:

Cox-2 inhibitors group:
 55 patients treated with cox-2 inhibitors out of which 11 patients also received NSAIDs, 10 patients also received steroids and 9 patients also received NSAIDs and steroids.

NSAIDs group:
 157 patients treated with NSAIDs out of which 39 patients also received steroids.

Steroids group:
 41 patients treated with steroids only

Comparison group:
 180 patients not treated with anti-inflammatory drugs, neither with cox-2 inhibitors, NSAIDs nor steroids. Further medication with analgesics was possible.

The baseline characteristics of the entire population into these four groups were comparable (Table 1). The patients received either placebo or the study medication at incremental doses from 10 to 150 mg. The proportion of patients receiving a co-medication with cox-2 inhibitors, NSAIDs, or steroids was equally distributed across all doses of the study drug. All patient groups were comparable regarding basic cardio-vascular criteria e.g. previous cardiological diseases, ECG criteria, hypertension or diabetes. As shown in Table 2, also the distribution of baseline NT-proBNP values was similar for the co-medication groups and also in relation to the number of patients with NT-proBNP values below or above the cut-off values of 125 pg/ml and 100 pg/ml.

During the observational period of 24 weeks, a total of 82 mild to serious CV-AEs were recorded. The relative incidence of CV AEs was significantly higher in the group which received cox-2 inhibitors. There was a trend towards a higher incidence of CV-AEs also in those patients who received NSAIDs. Risk for CV-AEs was 1.78-fold higher the use of cox-2 inhibitors (p=0.06). NT-proBNP<100 pg/ml did not predict an increased CV risk. In contrast, the risk for a CV adverse event predicted by NT-proBNP>100 pg/ml was 4.23-fold higher using cox-2 inhibitors (p=0.002), 1.6-fold higher using NSAIDs (p)=0.4) and 2.2-fold higher using steroids (p=0.09) (see Table 3).

Figure 2:
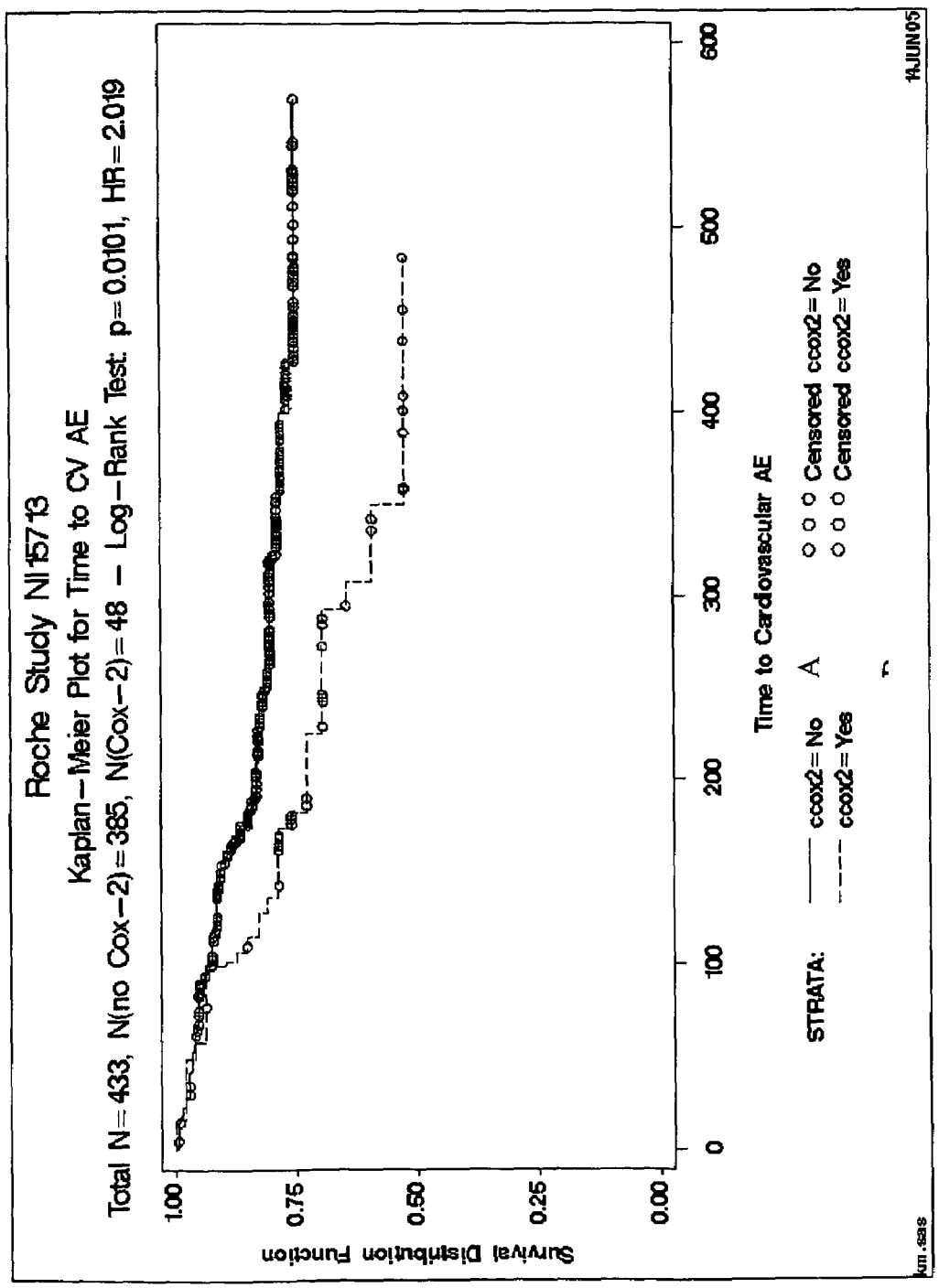
FIG. 2: This figure refers to Example 5. Kaplan-Meier curve to cardiovascular adverse events (CV-AEs) for cox-2 inhibitors group versus all patients without cox-2 inhibitor co-medication. Plotting cardiovascular adverse events over time as Kaplan-Meier curve demonstrates a higher risk in the cox-2 inhibitors group (ccox2=yes). All patients without cox-2 inhibitor co-medication (ccox2=no) in summary showed merely a minor cardiovascular risk. "censored" means that no CV-AE has been observed until the end of the observation time period. N, number; HR, hazard ratio; p, probability; ccox-2, concomitant cox-2 (means concomitant medication with cox-2 inhibitors); survival distribution function, event-free survival distribution function.

CV-AE rates were adjusted for study drug, age, and presence of diabetes. Rates of CV-AEs were significantly higher in cox-2 inhibitors group and there was a trend towards a higher incidence of CV-AEs in the NSAIDs group and the steroids group. Rates of CV-AEs were plotted over time for all groups (FIG. 2). The relative incidence of CV-AEs was significantly higher and occurred earlier in the cox-2 inhibitors group.

TABLE 1

Demographics and baseline values according to medication groups

|  | cox-2 inhibitors group | NSAIDs group | Steroids group | Comparison group |
|---|---|---|---|---|
| N | 55 | 157 | 41 | 180 |
| Age (mean ± SD) | 62 ± 9 | 59 ± 8 | 60 ± 9 | 62 ± 9 |
| Male (%) | 22 | 26 | 20 | 32 |
| Caucasian (%) | 96 | 89 | 95 | 88 |
| BMI (mean ± SD) | 31 ± 5 | 30 ± 5 | 31 ± 5 | 30 ± 5 |
| Prev./Conc. CV Dis. (%) | 22 | 23 | 32 | 29 |
| Diabetes mellitus (%) | 5 | 4 | 7 | 9 |
| Hypertension (%) | 31 | 27 | 29 | 35 |
| Stroke (%) | 0 | 1 | 2 | 3 |
| Systolic BP (mean ± SD) | 130 ± 14 | 131 ± 17 | 135 ± 17 | 133 ± 17 |
| Diastolic BP (mean ± SD) | 79 ± 9 | 80 ± 8 | 80 ± 9 | 80 ± 9 |
| Heart rate (mean ± SD) | 74 ± 8 | 73 ± 9 | 72 ± 9 | 72 ± 9 |
| PQ (mean ± SD) | 164 ± 26 | 161 ± 22 | 162 ± 27 | 163 ± 25 |
| QRS (mean ± SD) | 90 ± 15 | 90 ± 29 | 88 ± 17 | 87 ± 14 |
| QT (mean ± SD) | 400 ± 35 | 396 ± 32 | 399 ± 40 | 395 ± 35 |

N, number;
SD, standard deviation;
BMI, body mass index;
Prev./conc CV Dis., previous or concomitant cardiovascular dysfunction;
BP, blood pressure;
PQ, PQ-time;
QRS, QRS-complex;
QT, QT-time.

TABLE 2

NT-proBNP at baseline for co-medication groups

|  |  | cox-2 Inhibitors | Systemic NSAIDs | Steroids | Comparison group |
|---|---|---|---|---|---|
| N at baseline |  | 55 | 118 | 41 | 180 |
| NT-proBNP at | Mean ± SD | 125 ± 141 | 77 ± 78 | 118 ± 106 | 110 ± 131 |

TABLE 2-continued

NT-proBNP at baseline for co-medication groups

| | | cox-2 Inhibitors | Systemic NSAIDs | Steroids | Comparison group |
|---|---|---|---|---|---|
| baseline [pg/ml] | Median [Q1, Q3] | 83 [38, 187] | 55 [27, 94] | 77 [36, 196] | 63 [35, 139] |
| NT-proBNP at baseline1 <125 (%) | | 65 | 83 | 66 | 72 |
| NT-proBNP at baseline <100 (%) | | 60 | 73 | 59 | 66 |

N, number;
SD, standard deviation;
Q1, first quartile;
Q3, third quartile.

TABLE 3

CV AEs and Hazard Ratios (for Time to first AE) relative to the comparison group for cox-2 inhibitors group, NSAIDs group and Steroids groups

| | cox-2 inhibitors group | | | NSAIDs group | | | Steroids group | | | Comparison group | |
|---|---|---|---|---|---|---|---|---|---|---|---|
| | N | N (%) AEs | HR (vs comparison group) | N | N (%) AEs | HR (vs comparison group) | N | N(%) AEs | HR (vs comparison group) | N | N (%) AEs |
| All | 55 | 16 (29) | 1.784 (p = 0.06) | 157 | 27 (17) | 0.990 (p = 0.969) | 41 | 10 (24) | 1.530 (p = 0.243) | 180 | 29 (16) |
| NT-proBNP <100 pg/ml | 33 | 7 (21) | 1.059 (p = 0.895) | 114 | 19 (17) | 0.822 (p = 0.532) | 24 | 5 (21) | 1.106 (p = 0.840) | 118 | 22 (19) |
| NT-proBNP ≧100 pg/ml | 22 | 9 (41) | 4.233 (p = 0.002) | 43 | 8 (19) | 1.572 (p = 0.378) | 17 | 5 (29) | 2.165 (p = 0.089) | 62 | 7 (11) |
| HR (≧100 vs. 100) | | | 2.531 (p = 0.058) | | | 1.213 (p = 0.646) | | | 1.502 (p = 0.518) | | (0.621) (p = 0.268) |

N, number;
HR, hazard ratio;
AEs, adverse events;
p, probability

Table 4 shows the results of the multivariate regression analysis. Even after adjustment for age, sex and diabetes, an elevated NT-proBNP remained independently predictive for an adverse outcome when patients received a cox-2 inhibitor. A similar trend was seen when NSAIDs or steroids were given as rescue- or concomitant medication.

After adjustment for the study drug, age, history of hypertension or diabetes and for possible effects of anti-inflammatory co-medications, the risk for CV-AEs was 4.3-fold higher in the group receiving cox-2 inbitors with NT-proBNP>100 pg/ml compared with the comparison group without anti-inflammatory co-medication (p=0.0045) whereas in patients receiving cox-2 inhibitors with NT-proBNP values <100 pg/ml no increased risk for CV-AEs could be observed.

Even after adjustment for age, sex and diabetes, an elevated NT-proBNP remained independently predictive for an adverse outcome when patients received a cox-2 inhibitor. A similar trend was seen when NSAIDs or steroids were given as rescue- or concomitant medication.

TABLE 4

Multivariate Cox Regression analysis for Time to Cardiovascular Adverse Events in the cox-2 inhibitors group based on NT-proBNP 100 pg/ml

| Variables | Pr > Chi Square | Hazard Ratio | 95% LCL for HR | 95% UCL for HR |
|---|---|---|---|---|
| | | | Without other covariates | |
| NT-proBNP < 100; cox-2 inhibitors group vs. comparison group | 0.9565 | 1.024 | 0.437 | 2.399 |
| NT-proBNP > 100; cox-2 inhibitors group vs. comparison group | 0.0045 | 4.197 | 1.561 | 11.285 |
| NT-proBNP > 100 vs. NT-proBNP < 100; within comparison group | 0.2628 | 0.615 | 0.263 | 1.440 |
| NT-proBNP > 100 vs. NT-proBNP < 100; within cox-2 inhibitors group | 0.0672 | 2.521 | 0.937 | 6.785 |

TABLE 4-continued

Multivariate Cox Regression analysis for Time to Cardiovascular Adverse Events in the cox-2 inhibitors group based on NT-proBNP 100 pg/ml

| Variables | Pr > Chi Square | Hazard Ratio | 95% LCL for HR | 95% UCL for HR |
|---|---|---|---|---|
| | | With covariates | | |
| NT-proBNP < 100; cox-2 inhibitors group vs. comparison group | 0.9359 | 0.965 | 0.400 | 2.325 |
| NT-proBNP > 100; cox-2 inhibitors group vs. comparison group | 0.0045 | 4.338 | 1.575 | 11.954 |
| NT-proBNP > 100 vs. NT-proBNP < 100; within comparison group | 0.1827 | 0.549 | 0.227 | 1.326 |
| NT-proBNP > 100 vs. NT-proBNP < 100; within cox-2 inhibitors group | 0.0879 | 2.469 | 0.847 | 6.971 |
| Age >70 years | 0.3707 | 1.418 | 0.660 | 3.050 |
| Systolic blood pressure | 0.8488 | 1.072 | 0.524 | 2.196 |
| Diabetes mellitus | 0.1999 | 1.891 | 0.714 | 5.008 |
| Takes acetaminophen at baseline | 0.6064 | 0.653 | 0.129 | 3.302 |
| Takes NSAID at baseline | 0.4095 | 0.729 | 0.344 | 1.545 |

Pr > Chi Square, probability larger than Chi square;
LCL, lower confidential level;
UCL, upper confidential level;
HR, hazard ratio;

These results show that NT-proBNP allows to identify candidates for therapy with anti-inflammatory drugs who are at risk for CV AEs in the course or as a consequence of the therapy. It appears that the administration of anti-inflammatory drugs is safe in patients with NT-pro BNP values below the cut off level at baseline or at follow-up. Conversely, a level of NT-pro BNP>100 ng/ml or >125 pg/ml predicts a manifold higher risk to suffer a CV adverse events when taking cox-2 inhibitors or NSAIDs or steroids alone, or a combination of anti-inflammatory drugs.

What is claimed is:

1. A method for diagnosing an increased risk in a patient of suffering from a cardiovascular complication as a consequence of administration of a cox-2 selective inhibiting compound, said method comprising the steps of:
   (a) measuring a body fluid level of a natriuretic peptide selected from the group consisting of pre-proANP, proANP, NT-proANP, ANP, pre-proBNP, proBNP, NT-proBNP, and BNP, and
   (b) diagnosing the increased risk in the patient when the measured level of natriuretic peptide is greater than a known normal level.

2. The method according to claim 1, wherein the increased risk of a patient suffering from a cardiovascular complication as a consequence of administration of a cox-2 selective inhibiting compound is not due to an increase of blood volume or intravasal volume.

3. The method according to claim 1 wherein the natriuretic peptide is pre-proBNP, proBNP, NT-proBNP, or BNP.

4. The method according to claim 1, wherein the cox-2 selective inhibiting compound is selected from the group consisting of celecoxib, rofecoxib, etoricoxib, valdecoxib, parecoxib, and lumiracoxib.

5. The method according to claim 1, wherein additionally the level of at least one marker selected from the group consisting of markers of inflammation, markers of endothelial function, markers of ischemia, markers of thrombocyte activation, markers of atherosclerosis activation, and markers of intravascular activation of coagulation is measured.

6. The method according to claim 1, wherein the cardiovascular complication is selected from the group consisting of coronary heart disease, stable angina pectoris, acute coronary syndrome, unstable angina pectoris, myocardial infarction, ST-elevated myocardial infarction, non ST-elevated myocardial infarction, and stroke.

7. The method according to claim 1, wherein the body fluid is selected from the group consisting of urine, blood, blood plasma, and blood serum.

8. The method according to claim 7 wherein a blood plasma level of less than 80 pg/ml of NT-proBNP is associated with no increased risk of suffering from a cardiovascular complication.

9. The method according to claim 7 wherein a blood plasma level of less than 125 pg/ml of NT-proBNP is associated with no increased risk of suffering from a cardiovascular complication.

10. The method according to claim 7 wherein a blood plasma level of more than 125 and less than 500 pg/ml of NT-proBNP is associated with an increased risk of suffering from a cardiovascular complication.

11. The method according to claim 7 wherein a blood plasma level of more than 500 pg/ml of NT-proBNP is associated with a highly increased risk of suffering from a cardiovascular complication.

12. The method according to claim 1, wherein the level of the natriuretic peptide is measured using an array, a microfluidic device, a chemiluminescence analyzer, or a robotic device.

13. The method according to claim 1 wherein the level of the natriuretic peptide is measured using a specifically binding ligand selected from the group consisting of antibodies, nucleic acids, peptides, polypeptides, and aptamers.

14. A method for diagnosing an increased risk of cardiovascular complication in a patient who is a candidate for administration of a cox-2 selective inhibitor, said method comprising the steps of:
(a) measuring a body fluid level of a natriuretic peptide selected from the group consisting of pre-proANP, proANP, NT-proANP, ANP, pre-proBNP, proBNP, NT-proBNP, and BNP, and
(b) diagnosing the increased risk in the patient when the measured level of natriuretic peptide is greater than a known normal level.

15. The method according to claim 14, wherein the natriuretic peptide is NT-proBNP or BNP.

* * * * *